US008962890B1

(12) United States Patent
Tan et al.

(10) Patent No.: US 8,962,890 B1
(45) Date of Patent: Feb. 24, 2015

(54) MULTIFUNCTIONAL CROSSLINKERS FOR SHAPE-MEMORY POLYIMIDES, POLYAMIDES AND POLY(AMIDE-IMIDES) AND METHODS OF MAKING THE SAME

(71) Applicant: The United States of America, as represented by the Secretary of the Air Force, Washington, DC (US)

(72) Inventors: Loon-Seng Tan, Centerville, OH (US); David Huabin Wang, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/013,090

(22) Filed: Aug. 29, 2013

Related U.S. Application Data

(63) Continuation-in-part of application No. 13/557,326, filed on Jul. 25, 2012, now Pat. No. 8,546,614.

(60) Provisional application No. 61/636,134, filed on Apr. 20, 2012, provisional application No. 61/636,170, filed on Apr. 20, 2012.

(51) Int. Cl.
*C07C 211/02* (2006.01)
*C07C 215/00* (2006.01)
*C07C 213/02* (2006.01)

(52) U.S. Cl.
CPC ..................................... *C07C 213/02* (2013.01)
USPC ............................ 564/305; 564/441; 564/443

(58) Field of Classification Search
USPC .......................................... 564/305, 441, 443
See application file for complete search history.

(56) References Cited

U.S. PATENT DOCUMENTS

| 3,455,879 A | 7/1969 | Gay et al. |
| 3,514,415 A | 5/1970 | Karol |
| 3,600,361 A | 8/1971 | Heacock et al. |
| 3,732,200 A | 5/1973 | Bach |
| 3,763,211 A | 10/1973 | Heath et al. |
| 3,835,120 A | 9/1974 | Bach et al. |
| 3,925,312 A | 12/1975 | Fletcher et al. |
| 3,988,374 A | 10/1976 | Brode et al. |
| 4,107,125 A | 8/1978 | Lovejoy |
| 4,111,906 A | 9/1978 | Jones et al. |
| 4,203,922 A | 5/1980 | Jones et al. |
| 4,271,288 A | 6/1981 | Woo |
| RE30,922 E | 5/1982 | Heilman et al. |
| 4,394,499 A | 7/1983 | Robinson et al. |
| 4,535,101 A | 8/1985 | Lee et al. |
| 4,728,697 A | 3/1988 | Bolon et al. |
| 4,797,466 A | 1/1989 | Oikawa et al. |
| 4,981,497 A | 1/1991 | Hayes |
| 5,101,005 A | 3/1992 | Vora et al. |
| 5,101,037 A | 3/1992 | McGrath et al. |
| 5,175,234 A | 12/1992 | Lubowitz et al. |
| 5,205,894 A | 4/1993 | Ohta et al. |
| 5,278,276 A | 1/1994 | Ohta et al. |
| 5,300,559 A | 4/1994 | Sheehan et al. |
| 5,344,894 A | 9/1994 | Lubowitz et al. |
| 5,411,765 A | 5/1995 | Kanakarajan et al. |
| 5,508,377 A | 4/1996 | Yamashita et al. |
| 5,516,876 A | 5/1996 | Lubowitz et al. |
| 5,585,217 A | 12/1996 | Oba |
| 5,599,582 A | 2/1997 | Adamopoulos et al. |
| 5,610,265 A | 3/1997 | Tan et al. |
| 5,631,377 A | 5/1997 | Matsuo et al. |
| 5,670,651 A | 9/1997 | Tan et al. |
| 5,705,574 A | 1/1998 | Lubowitz et al. |
| 5,891,581 A | 4/1999 | Simpson et al. |
| 5,965,687 A | 10/1999 | Jensen |
| 6,001,277 A | 12/1999 | Ichimura et al. |
| 6,184,333 B1 | 2/2001 | Gray |
| 6,262,223 B1 | 7/2001 | Meador et al. |
| 6,307,008 B1 | 10/2001 | Lee et al. |
| 6,379,809 B1 | 4/2002 | Simpson et al. |
| 6,509,094 B1 | 1/2003 | Shah et al. |
| 7,402,264 B2 | 7/2008 | Ounaies et al. |
| 7,507,472 B2 | 3/2009 | Ounaies et al. |
| 7,527,751 B2 | 5/2009 | Ounaies et al. |
| 7,582,722 B1 | 9/2009 | Tan et al. |
| 7,588,699 B2 | 9/2009 | Park et al. |
| 7,678,873 B1 | 3/2010 | Tan et al. |
| 7,906,043 B2 | 3/2011 | Connell et al. |
| 7,935,414 B2 | 5/2011 | Ounaies et al. |
| 7,972,536 B2 | 7/2011 | Connell et al. |

(Continued)

FOREIGN PATENT DOCUMENTS

| EP | 233069 | 8/1987 |
| EP | 333406 | 9/1989 |

(Continued)

OTHER PUBLICATIONS

Tyan, Horng-Long. Effect of Reactivity of Organics-Modified Montmorillonite on the Thermal and Mechanical Properties of Montmorillonite/Polyimide Nanocomposites. Chem. Mater. 2001, 13, 222-226.*

Chao, Tsung-Yi. Nonlinear optical polyimide/montmorillonite nanocomposites consisting of azobenzene dyes, Dyes and Pigments. 77 (2008) 515-524.*

U.S. Patent and Trademark Office, Non-Final Office Action mailed Nov. 7, 2013, U.S. Appl. No. 13/546,439, 9 pages.

Japanese Patent Office, Machine Translation of JP 2005154643A, 39 pages.

(Continued)

*Primary Examiner* — Samantha Shterengarts
(74) *Attorney, Agent, or Firm* — AFMCLO/JAZ; Chastity Whitaker

(57) ABSTRACT

Multifunctional amine crosslinkers that may be used to create crosslinked polyimide, polyamide, and poly(amide-imide) polymers and films having shape memory properties at elevated temperatures and methods of making the same.

6 Claims, 5 Drawing Sheets

(56) References Cited

U.S. PATENT DOCUMENTS

| | | | |
|---|---|---|---|
| 8,034,893 | B2 | 10/2011 | Akiba et al. |
| 8,173,763 | B1 | 5/2012 | Tan et al. |
| 8,314,203 | B2 | 11/2012 | Tsutsumi et al. |
| 8,389,619 | B1 | 3/2013 | Tan et al. |
| 8,546,614 | B1 | 10/2013 | Tan et al. |
| 8,633,284 | B2 | 1/2014 | Ronk et al. |
| 8,785,589 | B1 | 7/2014 | Tan et al. |
| 8,791,227 | B1 | 7/2014 | Tan et al. |
| 2003/0064235 | A1 | 4/2003 | Okawa et al. |
| 2004/0233377 | A1 | 11/2004 | Utsumi et al. |
| 2005/0080229 | A1 | 4/2005 | Deets et al. |
| 2006/0057377 | A1 | 3/2006 | Harrison et al. |
| 2006/0217482 | A1 | 9/2006 | Lukehart et al. |
| 2006/0235194 | A1 | 10/2006 | Kato |
| 2006/0270825 | A1 | 11/2006 | Angermeier et al. |
| 2007/0106056 | A1 | 5/2007 | Itatani |
| 2007/0270562 | A1 | 11/2007 | Yamada et al. |
| 2007/0272124 | A1 | 11/2007 | Tsutsumi et al. |
| 2008/0025905 | A1 | 1/2008 | Wang et al. |
| 2008/0311303 | A1 | 12/2008 | Naiki et al. |
| 2009/0220722 | A1 | 9/2009 | Wang |
| 2010/0048745 | A1 | 2/2010 | Yamada et al. |
| 2011/0009513 | A1 | 1/2011 | Chaudhary et al. |
| 2011/0136061 | A1 | 6/2011 | Itatani |

FOREIGN PATENT DOCUMENTS

| | | |
|---|---|---|
| EP | 659802 | 6/1995 |
| EP | 397023 | 1/2009 |
| EP | 2380867 | 10/2011 |
| GB | 1147856 | 4/1969 |
| JP | 2005023151 | 1/2005 |
| JP | 2005154643 A | 6/2005 |
| WO | 2007086487 | 8/2007 |
| WO | 2009013376 | 1/2009 |

OTHER PUBLICATIONS

Meador, Mary Ann B., et al., "Improvements to the Synthesis of Polyimide Aerogels," ACS Spring National Meeting 2011, Anaheim, CA; Mar. 20-26, 2011, 34 pages.

Meador, Mary Ann B., et al., "Synthesis and Properties of Nanoporous Polyimide Aerogels Having a Covalently Bonded Network Structure," Polymer Preprints 2010, 51(1), 265.

Makita, Shohei, et al., "Synthesis of Alkaline-Developable, Photosensitive Hyperbranched Polyimides through the Reaction of Carboxylic Acid Dianhydrides and Trisamines," Journal of Polymer Science Part A: Polymer Chemistry, vol. 42, 3697-3707 (2004).

Lendlein Andreas et al., "Shape-Memory Polymers," Angewandte Chemie, International Edition, vol. 41, 2034-2057 (2002).

Liu C. et al., "Review of Progress in Shape-Memory Polymers," Journal of Materials Chemistry, vol. 17, 1543-1558 (2007).

Fay, Catherine C. et al., "Molecularly Oriented Polymeric Thin Films for Space Applications," High Performance Polymers, vol. 11, 145-156 (1999).

SRS Technologies and Mantech Materials, "Polyimides: CP1 and CP2 Film Properties," printed Jul. 9, 2012, 1 page, available at <http://www.mantechmaterials.com/_images/documents/3_8_doc.pdf>.

St. Clair, Anne K., et al. "Synthesis and Characterization of Essentially Colorless Polyimide Films," J. Polym. Mater. Sci Eng., vol. 51, pp. 62-66 (1984).

Miner, Gilda A., et al., "The Wettability of LaRC Colorless Polyimide Resins on Casting Surfaces," J. Polym. Mater. Sci Eng., vol. 76, pp. 381-382 (1997).

Wang, D.H., et al., "Photomechanical Response of Glassy Azobenzene Polyimide Networks," Macromolecules 2011, 44, pp. 3840-3846.

Pyun, Eumi, et al., "Kinetics and mechanisms of thermal imidization of a polyamic acid studied by ultraviolet-visible spectroscopy", Macromolecules (1989), 22(3), 1174-83.

Hosono, Nobuhiko, et al., "Photochemical control of network structure in gels and photo-induced changes in their viscoelastic properties" Colloids and Surfaces, B: Biointerfaces (2007), 56(1-2), 285-289.

Zhang, Chaohui, et al., "Rapid bending of a nonliquid crystal azobenzene polymer film and characteristics of surface relief grating" Journal of Applied Polymer Science (2009), 113(2), 1330-1334.

Hergenrother, P.M., "Recent Developments in High Temperature Organic Polymers," Polyimides and Other High-Temperature Polymers, Abadie, M.J.M. and Sillion, B., Eds., Elsevier: New York, 1991, pp. 1-18.

Agolini, F., et al., "Synthesis and Properties of Azoaromatic Polymers," Macromolecules (May-Jun. 1970), vol. 3, No. 3, 349-351.

White, T.J., et al., "A high frequency photodriven polymer oscillator," J. Soft Matter 2008,4, 1796-1798.

White, T.J., et al., "Polarization-controlled, photodriven bending in monodomain liquid crystal elastomer cantilevers," J. Mater. Chem. 2009, 19, 1080-1085.

Lee, K.M., et al., "Relationship between the Photomechanical Response and the Thermomechanical Properties of Azobenzene Liquid Crystalline Polymer Networks," Macromolecules 2010, 43, 8185-8190.

Sroog, C.E., "Polyimides," Prog. Polym. Sci. 1991, 16, 561-694.

Koshiba, Y., et al., "Photo-induced alignment behavior of azobenzene compound in thin film," Thin Solid Films 2009, 518, 805-809.

Koerner, H., et al., "Photogenerating work from polymers," Mater. Today (Oxford, U. K.) 2008, 11, (7-8), 34-42.

Wang, D.H., et al., "Nanocomposites Derived from a Low-Color Aromatic Polyimide (CP2) and Amine-Functionalized Vapor-Grown Carbon Nanofibers: In Situ Polymerization and Characterization," Macromolecules 2007, 40, 6100-6111.

Arlen, M., et al., "Thermal-Electrical Character of in Situ Synthesized Polyimide-Grafted Carbon Nanofiber Composites," Macromolecules 2008, 41, 8053-8062.

Lee, Kyung Min, and White, Timothy J., "Photomechanical Response of Composite Structures Built from Azobenzene Liquid Crystal Polymer Networks," Polymers (2011), 3, 1447-1457.

Behl, Marc, et al., "Shape-memory polymers" Materials Today (Oxford, United Kingdom) (2007), 10(4), 20-28.

Xie, Tao, "Recent advances in shape memory polymer," Polymer (2011), 52(22), 4985-5000.

Liu, C., et al., "Review of progress in shape-memory polymers," Journal of Materials Chemistry (2007), 17(16), 1543-1558.

Koerner, Koerner, et al., "Polymer design for high temperature shape memory: Low crosslink density polyimides," Polymer(2013), 54, 391-402.

Shumaker, J.A., et al, "Synthesis of high temperature polyaspartimide-urea based shape memory Polymers," Polymer (2012), 53, 4637-4642.

Jeong, K.U., et al., "Adhesion property of novel polyimides containing fluorine and phosphine oxide moieties" J. Adhesion Sci. Technol., vol. 15, No. 14, pp. 1787-1803 (2001).

Whitaker, Craig M., et al., "Synthesis and Solid-state Structure of Substituted Arylphosphine Oxides," Journal of Organic Chemistry (1995) 60, 3499-3508.

Sinou, Denis, et al., "Synthesis of a Family of Triarylphosphanes with Fluorous Phase Affinity," European J. Org. Chem. 2002, 269-275.

Schuh, Christian, et al., "Shape-Memory Properties of Segmented Polymers Containing Aramid Hard Segments and Polycaprolactone Soft Segments," Polymers 2010, 2, 71-85.

Rabani, Gouher, et al, "Synthesis and characterization of two shape-memory polymers containing short aramid hard segments and poly(3-caprolactone) soft segments," Polymer (2006) 47, 4251-4260.

Straub, Darel K., "Lewis Structures of Boron Compounds Involving Multiple Bonding," Journal Chem. Ed., 72(6), (1995), 494-497.

Chao, Tsung-Yi, et al., "Nonlinear optical polyimide/montmorillonite nanocomposites consisting of azobenzene dyes," Dyes and Pigments 77 (2008) 515-524.

Tan, Loon-Seng, et al., U.S. Appl. No. 13/546,439, filed Jul. 11, 2012.

Tan, Loon-Seng, et al., U.S. Appl. No. 13/866,524, filed Apr. 19, 2013.

Tan, Loon-Seng, et al., U.S. Appl. No. 13/866,551, filed Apr. 19, 2013.

United States Patent and Trademark Office, Non-Final Office Action in Related Case, U.S. Appl. No. 13/557,326, Mail Date Sep. 26, 2012.

(56) References Cited

OTHER PUBLICATIONS

United States Patent and Trademark Office, Non-Final Office Action in Related Case, U.S. Appl. No. 13/557,326, Mail Date Mar. 27, 2013.
U.S. Patent and Trademark Office, Non-Final Office Action mailed Feb. 10, 2014, U.S. Appl. No. 13/866,551, 5 pages.
Park et al., "Actuating single wall carbon nanotube-polymer composites: intrinsic unimorphs," Adv. Mater., vol. 20 (2008) 2074-2079.
Serak et al., "Azobenzene liquid crystal polymer-based membrane and cantilever optical systems," Optics Express, vol. 17 (2009) 15736-15746.
Tabiryan et al., "Polymer film with optically controlled form and actuation," T. Opt. Exp., vol. 13 (2005) 7442-7448.
Usami et al., "Photo-aligned blend films of azobenzene-containing polyimides with and without side-chains for inducing inclined alignment of liquid crystal molecules," J. Appl. Phys., vol. 110 (2011) 043522/1-043522/6.
Van Oosten et al., "Bending dynamics and directionality reversal in liquid crystal network photoactuators," Macromol., vol. 41 (2008) 8592-8596.
Van Oosten et al., "Glassy photomechanical liquid-crystal network actuators for microscale devices," Eur. Phys. J. E., vol. 23 (2007) 329-336.
Viswanathan et al., "Surface relief structures on azo polymer films," J. Mater. Chem., vol. 9 (1999) 1941-1955.
Young et al., "Molecular modeling of the poling of piezoelectric polyimides," Polym., vol. 40 (1999) 2787-2795.
Yu et al., "Photomechanical effects of ferroelectric liquid-crystalline elastomers containing azobenzene chromophores," Angew. Chem. Int'l. Ed., vol. 46 (2007) 881-883.
Yu et al., "Effect of cross-linking density of photoinduced bending behavior of oriented liquid-crystalline network films containing azobenzene," Chem. Mater., vol. 16 (2004) 1637-1643.
Amaranatha Reddy et al., "Occurrence of the B7 mesophase in two homologous series of seven-ring achiral compounds composed of banana-shaped molecules," Liq. Cryst., vol. 30 (2003) 273-283.
Barrett et al., "Photo-mechanical effects in azobenzene-containing soft materials," J. Soft Mater., vol. 3 (2007) 1249-1261.
Gonzalo et al., "Synthesis, Characterization, and Thermal Properties of Piezoelectric Polyimides," J. Polym. Sci. Part A: Polym. Chem., vol. 47 (2009) 722-730.
Hamciuc et al., "Aromatic polyimides containing polar nitrile groups," Revue Rourmaine de Chimie, vol. 51 (2006) 765-771.
Hamciuc et al., "Study of thin films made from poly(amide-imide)s containing nitrile groups," Int'l. Semicond. Conf., vol. 2 (2010) 341-344.
Hamciuc et al., "Hybrid films based on a polyimide containing nitrile groups and barium and titanium oxides," High Pert. Polym., vol. 22 (2010) 225-236.
Hamciuc et al., "Aromatic poly(ether imide)s containing nitrile groups," High Pert. Polym., vol. 21 (2009) 205-218.
Chen et al., "Highly stable optically induced birefringence and holographic surface gratings on a new azocarbazole-based polyimide," Macromol., vol. 32 (1995) 8572-8579.
Jacobs et al., "Dielectric characteristics of polyimide CP2," Polym., vol. 51 (2010) 3139-3146.
Cojocariu et al., "Ligh-induced motions in azobenzene-containing polymers," Pure Appl. Chem., vol. 76 (2004) 1479-197.
Kang et al., "Synthesis and characterization of polyimides from unsymmetrical diamine with cyano groups," Polym. J., vol. 33 (2001) 284-289.
Klein et al., "Synthesis and characterization of polyimides derived from cyano-containing 1,4-bis(4-aminophenoxy) benzene monomers," Polym. Bull., vol. 59 (2007) 1-12.
Georgiev et al., "Polyimide coatings containing azo-chromophores as structural units," J. Physics Conf. Ser., vol. 113 (2008) 012032.
Eisenbach et al., "Isomerization of aromatic azo chromophores in poly(ethyl acrylate) networks and photomechanical effect," Polymer, vol. 21 (1980) 1175-1179.

Koton et al, "Polyimides containing different heterocyclic unites in the main chain," Chem. Abstr. 20532k, vol. 96 (1982).
Koton et al, "Polyimides containing various heterocyclic main-chain units," Polym. Sci., vol. 23 (1981) 1909-1915.
Lee et al., "Enhancement of photogenerated mechanical force in azobenzene-functionalized polyimides," Angew. Chem., vol. 124 (2012) 4193-4197.
Li et al., "Synthesis and characterization of new polyimides containing nitrile groups," High Perf. Polym., vol. 17 (2005) 135-147.
Liaw et al., "High glass transitions of new polyamides, polyimides, and poly(amide-imide)s containing a triphenylamine group: synthesis and characterization," Macromol., vol. 35 (2002) 4669-4676.
Liaw et al., "Novel organosoluble poly(pyridine-imide) with pendent pyrene group: synthesis, thermal, optical, electrochemical, electrochromic, and protonation characterization," Macromol., vol. 40 (2007) 3568-3574.
Liaw et al., "Novel poly(pyridine imide) with pendent naphthalene groups: synthesis and thermal, optical, electrochemical, electrochromic, and protonation characterization," J. Polym. Sci. Part A: Polym. Chem., vol. 45 (2007) 2367-2374.
Machine, Translation of WO 2009/013376 as provided by WIPO Patentscope, Powered by Google Translate, accessed on Sep. 30, 2014.
Machine, Translation of JP 2005-023151 as provided by Patent Abstracts of Japan, accessed on Oct. 6, 2014.
Finkelmann et al., "A new opto-mechanical effect in solids," Phys. Rev. Lett., vol. 87 (2001) 01550111-01550114.
Sakamoto et al., "Highly polarized polymer-based light-emitting diodes fabricated by using very thin photoaligned polyimide layers," J. Appl. Phys., vol. 107 (2010) 113108.
Sakamoto et al., " Light exposure dependence of molecular orientation of glassy polyfluorene layers formed on photo-aligned polyimide films," Colloids Surf. B: Bioint., vol. 56 (2007) 260-264.
Mercer et al., "Synthesis and properties of new alternating copolyethers containing pendent cyano groups," Polym., vol. 34 (1994) 5355-5363.
Ounaies et al., "Structure-property study of piezoelectricity in polyimides," Proc. SPIE, vol. 3669 (1999) 171-178.
Park et al., "In situ poling and imidization of amorphous piezoelectric polyimides," Polym., vol. 45 (2004) 5417-5425, as provided in ICASE Report No. 2002-39.
Harris et al., "Large amplitude light-induced motion in high elastic modulus polymer actuators," J. Mater. Chem., vol. 15 (2005) 5043-5048.
Saxena et al., "Synthesis and characterization of polyamides and poly(amide-imide)s derived from 2,6-bis(3-aminophenoxy)benzonitrile or 2,6-bis(4-aminophenoxy)benzonitrite," Polym. Int'l., vol. 54 (2005) 544-552.
He et al., "Degenerate two-photon-absorption spectral studies of highly two-photon active organic chromophores," J. Chem. Phys., vol. 120 (2004) 5275-5284.
Hogan et al., "UV-manipulation of order and macroscopic shape in newmatic elastomers," Phys. Rev. E. Stat. Nonlinear. Sof. Mater. Phys., vol. 65 (2008) 041720001-0417201 10.
Hrozhyk et al., "Bidirectional photoresponse of surface pretreated azobenzene liquid crystal polymer networks," Optics Express, vol. 17 (2009) 716-722.
Hugel et al., "Single-molecule optomechanical cycle," Science, vol. 496 (2002) 1103-1106.
Irie, "Photochromism and molecular mechanical devices," Bull. Chem. Soc. Japan, vol. 81 (2008) 917-926.
Usami et al., "Improvement in photo-alignment efficiency of azobenzene-containing polyimide films," Thin Solid Films, vol. 518 (2009) 729-734.
Usami et al., "Pretilt angle control of liquid crystal molecules by photoaligned films of azobenzene-containing polyimide with a different content of side-chain," J. Appl. Phys., vol. 104 (2008) 113528.
United States Patent and Trademark Office, Non-Final Office Action in U.S. Appl. No. 13/661,194, mailed Jul. 2, 2014, 7 pages total.
Jenekhe et al., "Nonlinear optical properties of poly(p-phenylenebenzoisoxazole)," Chem. Mater., vol. 4 (1992) 683-687.

(56) References Cited

OTHER PUBLICATIONS

Wang et al., "High-temperature dielectric polyimide films for energy storage applications," MRS Online Proc. Lib., vol. 1541 (2013) 6 pages total.

Wang et al., "Synthesis of symmetric and asymmetric polyimides containing benzonitrile groups for dielectric applications," Polym. Prints, vol. 51 (2010) 522-533.

Wang et al., "Synthesis and characterization of unsymmetrical benzonitrile-containing polyimides: viscosity-lowering effect and dielectric properties," J. Polym. Sci. Part A: Polym. Chem., vol. 51 (2013) 4998-5100.

Kannan et al., " Diphenylaminofluorene-based two-photon-absorbing chormophores with various pi-electron acceptors," Chem. Mater, vol. 13 (2001) 1896-1904.

Kannan et al., "Toward highly active two-photon absorbing liquids. Synthesis and Characterization of 1,3,5-Triazine-based octupolar molecules," Chem. Mater., vol. 16 (2004) 185-14.

Kondo et al., "Effect of concentration of photoactive chromophores on photomechanical properties of crosslinked azobenzene liquid-crystalline polymers," J. Mater. Chem., vol. 20 (2010) 117-122.

Kumar et al., "Photochemistry of azobenzene-containing polymers," Chem. Rev., vol. 89 (1989) 1915-1925.

Li et al., "Light-driven side-on nematic elastomer actuators," Adv. Mater., vol. 15 (2003) 568-572.

Lovrein, "The photoviscosity effect," PNAS, vol. 57 (1967) 236-242.

Natansohn et al., "Photoinduced motions in azo-containing polymers," Chem. Rev., vol. 201 (2002) 4139-4175.

\* cited by examiner

X

1-chloro-2-methyl-4-nitro-benzene
(R is meta to nitro group)

XI

1-(trifluoromethyl)-2-chloro-4-nitro-benzene
(R is para to nitro group)

XII

1,1,1-tris[4-(2-trifluoromethyl-5-aminophenoxy)phenyl]ethane
(R is para to the primary amine)

XIII tris[4-(2-chloro-4-aminophenoxy)phenyl]amine
(R is meta to the primary amine)

tris[4-(2-methyl-4-aminophenoxy)phenyl] borate
(R meta to the primary amine)

tris[4-(2-fluoro-5-aminophenoxy)phenyl] phosphine oxide
(R para to the primary amine)

MULTIFUNCTIONAL CROSSLINKERS FOR SHAPE-MEMORY POLYIMIDES, POLYAMIDES AND POLY(AMIDE-IMIDES) AND METHODS OF MAKING THE SAME

CROSS-REFERENCE TO RELATED APPLICATIONS

This application is a continuation-in-part of U.S. patent application Ser. No. 13/557,326, filed Jul. 25, 2012, which claims the benefit of U.S. Provisional Patent Application No. 61/636,134, filed on Apr. 20, 2012, and U.S. Provisional Patent Application No. 61/636,170, filed Apr. 20, 2012, all of which are incorporated herein by reference in their entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of multifunctional crosslinkers. More particularly, it relates to tri- and tetrafunctional amine crosslinkers that may be used to create crosslinked polyimide, polyamide, and poly(amide-imide) polymers and films having shape memory properties at elevated temperatures and methods of making the same.

2. Description of the Related Art

Shape memory materials, including shape memory polymers (SMPs) and shape memory alloys (SMAs) are a class of active materials that can be programmed to "fix" a temporary shape or a series of temporary shapes and to recover to a "memorized" permanent shape upon application of a predetermined external stimulus. The permanent shape of most SMPs is established during the manufacturing process by a network of covalent or physical crosslinking. While the shape memory effects of SMAs stem from martensitic/austenitic transitions (changes in crystal structure), the shape memory effect of thermally-induced SMPs is driven by heating the polymer above its glass transition temperature ($T_g$) or melting point ($T_m$), which causes the SMP to become soft and elastomeric in nature. The heated SMP may be deformed into one or more temporary shapes. The SMP is then cooled below the $T_g$ or $T_m$ while still under stress, causing immobilization of the constituent network chains to fix the temporary shape. Recovery of the permanent shape is then accomplished by heating the SMP above the $T_g$ or $T_m$, which remobilizes the network chains and allows rubber (entropic) elasticity to return the SMP to its equilibrium or permanent shape. Corresponding to the nature of the external stimulus, other types of SMPs include light-induced, electro-active, pH-responsive, and water/moisture-driven SMPs.

SMPs and SMAs have been widely used in actuation, robotics, and piping, as components in aircraft and automobiles, and in medical and dental applications. SMPs possess many properties that make them more attractive than SMAs, such as much lower cost, easier manufacturing and processing using conventional methods, higher capacities for elastic deformation (up to 200% in most cases), lower density, and a broader range of customizable application temperatures. In addition, many SMPs have the potential for biocompatibility and biodegradability. However, most currently available SMPs consist of high-alkyl content polymers such as polyurethane, poly(ε-caprolactone), poly(norbornene), (ethylene-oxide)/(ethylene terephthalate)-based copolymers, styrene/butadiene copolymers, thiolene/acrylate copolymers, etc. Many of these SMPs do not possess shape memory properties above 150° C., nor do they possess long-term thermal and thermo-oxidative stability in this temperature region.

Aromatic polyimides, polyamides, and poly(amide-imides) are common classes of heat-resistant, thermally stable polymers with glass-transition temperatures in the excess of 150° C. The solubility of the polymers in common organic solvents may be improved by introducing wholly aromatic groups containing meta-phenoxyphenol (—$OC_6H_4$—$OC_6H_5$) or meta-oxyphenylene-meta-oxyphenoxy (—$OC_6H_4O$—$C_6H_4O$—) moieties to the main chains or side chains of the polymer backbones. The addition of crosslinkers introduces a covalent network structure into these polymers, which imparts programmable shape-memory effects.

SUMMARY OF THE INVENTION

The present invention includes a trifunctional crosslinker having the following general structure A, in which W is selected from a group consisting of $CH_3C$, N, P=O, or $BO_3$ (which may alternatively be written as B(—O)$_3$), with R being selected from a group consisting of —F, —Cl, —$CF_3$, or —$CH_3$ and the amine groups ($NH_2$) being located meta or para with respect to R:

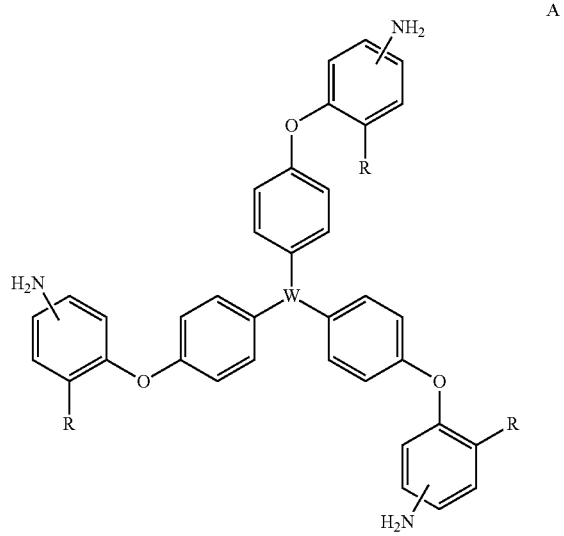

The present invention further includes a method for synthesizing the trifunctional crosslinker having general structure A in which W is selected from the group consisting of $CH_3C$, N, and B(—O)$_3$, the method comprising the steps of: mixing, in a polar, aprotic solvent, potassium carbonate, a tris(hydroxyphenyl) compound that is selected from the group consisting of 1,1,1-tris(4-hydroxyphenyl)ethane, tris (4-hydroxyphenyl)amine, and tris(4-hydroxyphenyl)borate, and a halogenated nitrobenzene having the following general structure:

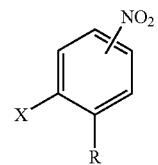

in which X is a halogen such as —F or —Cl; R is —H, —F, —Cl, —CF$_3$, or —CH$_3$; and the nitro group (—NO$_2$) is either meta or para with respect to R. A tris(nitrophenoxy)phenyl compound is formed by this mixture. The method concludes with reducing the tris(nitrophenoxy)phenyl compound by catalytic hydrogenation in the presence of 5% palladium on activated carbon in a hydrogen atmosphere to form the trifunctional crosslinker.

In one embodiment of the method, the halogenated nitrobenzene is selected from the group consisting of 1-fluoro-4-nitro-benzene, 1-chloro-4-nitro-benzene, 1,2-difluoro-4-nitro-benzene, 1,2-dichloro-4-nitro-benzene, 1-fluoro-2-methyl-4-nitro-benzene, 1-chloro-2-methyl-4-nitro-benzene, 1-fluoro-2-(trifluoromethyl)-4-nitro-benzene, 1-chloro-2-(trifluoromethyl)-4-nitro-benzene, 1-methyl-2-chloro-4-nitrobenzene, 1-methyl-2-fluoro-4-nitro-benzene, 1-(trifluoromethyl)-2-chloro-4-nitro-benzene, 1-methyl-2-fluoro-4-nitro-benzene.

In another embodiment, W is CH$_3$C, and the trifunctional crosslinker is selected from the group consisting of 1,1,1-tris[4-(2-fluoro-5-aminophenoxy)phenyl]ethane, 1,1,1-tris[4-(2-fluoro-4-aminophenoxy)phenyl]ethane, 1,1,1-tris[4-(2-chloro-5-aminophenoxy)phenyl]ethane, 1,1,1-tris[4-(2-chloro-4-aminophenoxy)phenyl]ethane, 1,1,1-tris[4-(2-trifluoromethyl-5-aminophenoxy)phenyl]ethane, 1,1,1-tris[4-(2-trifluoromethyl-4-aminophenoxy)phenyl]ethane, 1,1,1-tris[4-(2-methyl-5-aminophenoxy)phenyl]ethane, and 1,1,1-tris[4-(2-methyl-4-aminophenoxy)phenyl]ethane.

In yet another embodiment, W is N, and the trifunctional crosslinker is selected from the group consisting of tris[4-(4-aminophenoxyl)phenyl]amine, tris[4-(2-fluoro-5-aminophenoxy)phenyl]amine, tris[4-(2-fluoro-4-aminophenoxy)phenyl]amine, tris[4-(2-chloro-5-aminophenoxy)phenyl]amine, tris[4-(2-chloro-4-aminophenoxy)phenyl]amine, tris[4-(2-trifluoromethyl-5-aminophenoxy)phenyl]amine, tris[4-(2-trifluoromethyl-4-aminophenoxy)phenyl]amine, tris[4-(2-methyl-5-aminophenoxy)phenyl]amine, and tris[(4-(2-methyl-4-aminophenoxy)phenyl]amine.

In a further embodiment, W is B(—O)$_3$, and the trifunctional crosslinker is selected from the group consisting of tris[4-(4-aminophenoxyl)phenyl]borate, tris[4-(2-fluoro-5-aminophenoxy)phenyl]borate, tris[4-(2-fluoro-4-aminophenoxy)phenyl]borate, tris[4-(2-chloro-5-aminophenoxy)phenyl]borate, tris[4-(2-chloro-4-aminophenoxy)phenyl]borate, tris[4-(2-trifluoromethyl-5-aminophenoxy)phenyl]borate, tris[4-(2-trifluoromethyl-4-aminophenoxy)phenyl]borate, tris[4-(2-methyl-5-aminophenoxy)phenyl]borate, and tris[4-(2-methyl-4-aminophenoxy)phenyl]borate.

The present invention further includes a method for synthesizing the trifunctional crosslinker having general structure A in which W is P=O, the method comprising the steps of: oxidizing tris(4-methoxyphenyl)phosphine with aqueous hydrogen peroxide to form tris(4-methoxyphenyl)phosphine oxide; demethylating the tris(4-methoxyphenyl)phosphine oxide by heating in pyridine hydrochloride to form tris(4-hydroxyphenyl)phosphine oxide; mixing, in a polar, aprotic solvent, the tris(4-hydroxyphenyl)phosphine oxide, potassium carbonate, and a halogenated nitrobenzene having the following general structure:

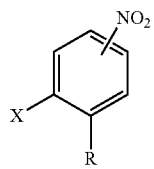

in which X is a halogen such as —F or —Cl; R is —H, —F, —Cl, —CF$_3$, or —CH$_3$; and the nitro group (—NO$_2$) is either meta or para with respect to R. A tris(nitrophenoxy)phenyl phosphine oxide compound is formed by this mixture. The method concludes with reducing the tris(nitrophenoxy)phenyl phosphine oxide compound by catalytic hydrogenation in the presence of 5% palladium on activated carbon in a hydrogen atmosphere to form the trifunctional crosslinker.

In one embodiment of the method in which W is P=O, the halogenated nitrobenzene is selected from the group consisting of 1-fluoro-4-nitro-benzene, 1-chloro-4-nitro-benzene, 1,2-difluoro-4-nitro-benzene, 1,2-dichloro-4-nitro-benzene, 1-fluoro-2-methyl-4-nitro-benzene, 1-chloro-2-methyl-4-nitro-benzene, 1-fluoro-2-(trifluoromethyl)-4-nitro-benzene, 1-chloro-2-(trifluoromethyl)-4-nitro-benzene, 1-methyl-2-chloro-4-nitrobenzene, 1-methyl-2-fluoro-4-nitro-benzene, 1-(trifluoromethyl)-2-chloro-4-nitro-benzene, 1-methyl-2-fluoro-4-nitro-benzene.

In another embodiment of the method in which W is P=O, the trifunctional crosslinker is selected from the group consisting of tris[(4-aminophenoxy)phenyl]phosphine oxide, tris[4-(2-fluoro-5-aminophenoxy)phenyl]phosphine oxide, tris[4-(2-fluoro-4-aminophenoxy)phenyl]phosphine oxide, tris[4-(2-chloro-5-aminophenoxy)phenyl]phosphine oxide, tris[4-(2-chloro-4-aminophenoxy)phenyl]phosphine oxide, tris[4-(2-trifluoromethyl-5-aminophenoxy)phenyl]phosphine oxide, tris[4-(2-trifluoromethyl-4-aminophenoxy)phenyl]phosphine oxide, tris[4-(2-methyl-5-aminophenoxy)phenyl]phosphine oxide, and tris[4-(2-methyl-4-aminophenoxy)phenyl]phosphine oxide.

DETAILED DESCRIPTION OF THE INVENTION

Figure 1:
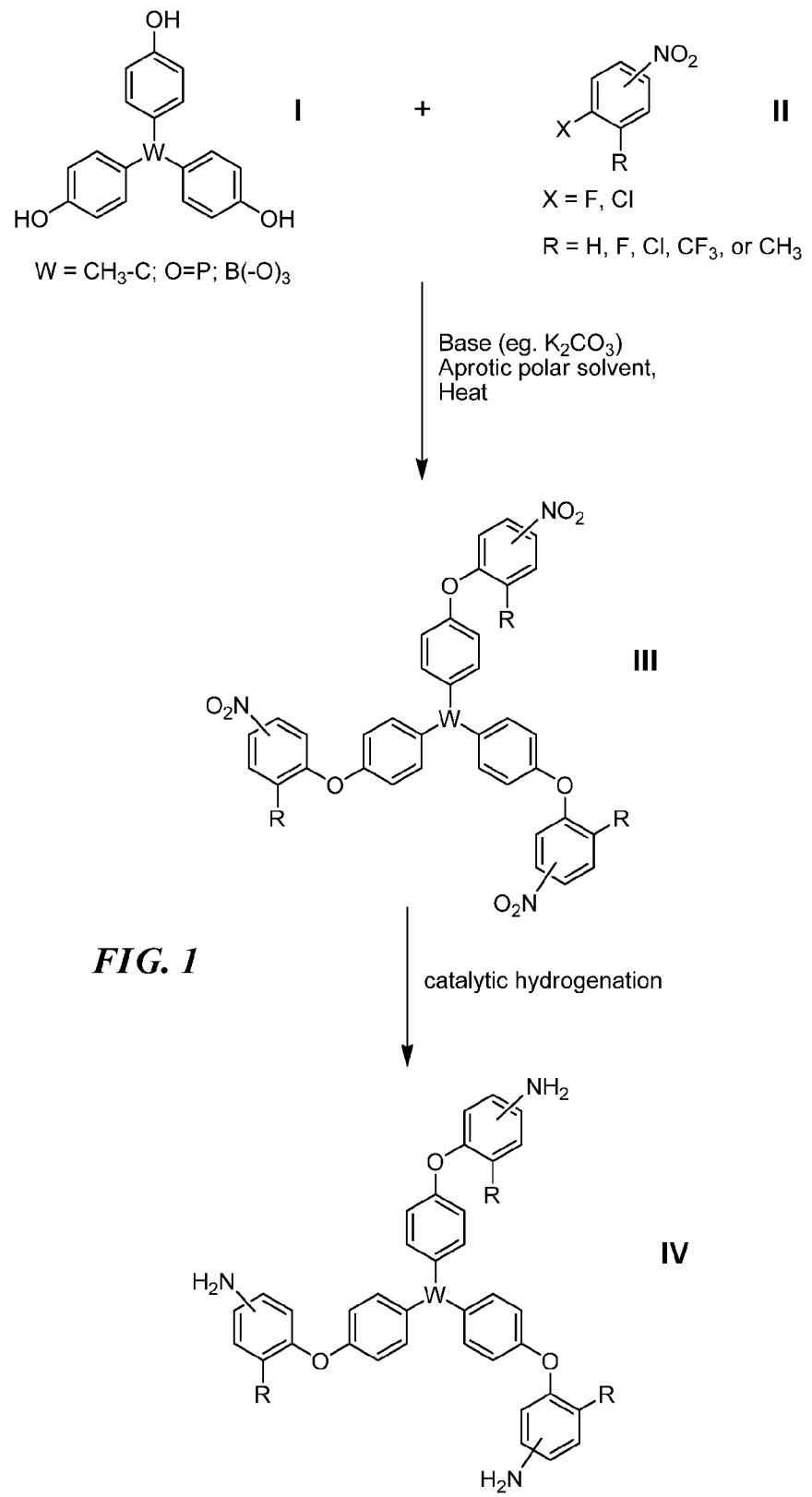
FIG. 1 illustrates an exemplary method for synthesizing triamine crosslinkers according to the present invention.

The present invention relates to multi-amine compounds that may be used to crosslink polyimides, polyamides, and poly(amide-imides) to create a covalent network structure that results in shape memory effects at elevated temperatures. The tetrahedral geometry and diphenylether linking groups of the presently disclosed tri- and tetrafunctional amine crosslinkers allow the synthesis of crosslinked polymers with both high-temperature tolerance and conformational flexibility. The present invention further includes methods of making the trifunctional amine crosslinkers.

The synthesis of a polyimide is typically accomplished by polymerization of a diamine and a dianhydride in a 1:1 molar ratio to generate a poly(amic acid) precursor, which is then converted to the corresponding polyimide typically by either thermal cure (heating to >200° C. in solution or solid state) or chemical imidization using a dehydrating agent or promoter such as acetic anhydride/triethylamine or acetic anhydride/pyridine. To generate a polyimide having the desired amount of crosslinking, an anhydride-terminated poly(amic acid)

precursor is first generated by off-setting the dianhydride:diamine ratio so that the amount of dianhydride is in excess to cap both ends of the poly(amic acid) precursor. An appropriate amount of a multifunctional amine crosslinker is then be added to the precursor solution so that all the terminal anhydride groups will be consumed. Crosslinked polyimides may then be created using appropriate imidization conditions.

The synthesis of a polyamide is typically accomplished by two general methods. The first method involves polymerization of a diamine and a diacid chloride in a 1:1 molar ratio in an amide solvent such as N,N-dimethylformamide (DMF), N,N-dimethylacetamide (DMAc), N-methylpyrrolidone (NMP), etc. To generate a polyamide having the desired amount of crosslinking, an acid-chloride-terminated polymer is first generated by off-setting the diacid chloride:diamine ratio so that the amount of diacid chloride is in excess to cap both ends of the polymer. Subsequent addition of a multifunctional amine crosslinker in appropriate amounts to the acid-chloride-terminated polymer so that all the terminal acid chloride groups are consumed, immediately followed by casting and thermal curing under reduced pressure, leads to the crosslinked polyamide films.

The second method of synthesizing a polyamide involves polymerization of a diamine and a dicarboxylic acid with the aid of a promoter/catalyst combination such as triethylphosphite/pyridine (via Yamazaki-Higashi reaction) in an amide solvent such as N,N-dimethylformamide (DMF), N,N-dimethylacetamide (DMAc), N-methylpyrrolidone (NMP), etc. To generate a polyamide having the desired amount of crosslinking, a carboxylic acid-terminated polymer is first generated by off-setting the diacid:diamine ratio so that the amount of diacid monomer is in excess to cap both ends of the polymer. After the carboxylic acid-terminated polyamide has been isolated by precipitation in water and filtration, it is washed (water & methanol) and dried. It is then redissolved in an amide solvent and mixed with an amide solution of a multifunctional amine crosslinker in appropriate amounts so that all the terminal carboxylic-acid groups are consumed, which is immediately followed by casting and thermal curing under reduced pressure to create crosslinked polyamide films.

The synthesis of a poly(amide-imide) is typically accomplished by polymerization of a diamine and a trimellitic anhydride (TMA) or a dicarboxylic acid monomer derived from trimellitic anhydride aided by triethylphosphite/pyridine (Yamazaki-Higashi reagent) in a 1:1 molar ratio in an amide solvent such as N,N-dimethylformamide (DMF), N,N-dimethylacetamide (DMAc), N-methylpyrrolidone (NMP) etc. To generate a poly(amide-imide) having the desired amount of crosslinking, it is more suitable that a anhydride-terminated poly (amide-imide) is first generated via Yamazaki-Higashi reaction by off-setting TMA:diamine ratio so that the amount of TMA monomer is in excess to cap both ends of the polymer. After the anhydride-terminated polyamide has been isolated by precipitation in methanol and filtration, it is washed with methanol and dried in vacuo at 200° C. overnight. It is then redissolved in an amide solvent and mixed with an amide solution of a multifunctional amine crosslinker in appropriate amounts so that all the terminal carboxylic-acid groups are consumed, which is immediately followed by casting and thermal curing under reduced pressure to create crosslinked poly(amide-imide) films. Persons of skill in the art will appreciate that this polymerization method may be applied to other dianhydride monomers containing preformed aromatic amide moieties.

A triamine crosslinker according to the present invention exhibits the following general structure A, in which W is $CH_3C$ (methylcarbyl), N (trivalent nitrogen), P=O (phosphine oxide), or $BO_3$ (borate; may also be written as B(—O)$_3$); R is —H, —F, —Cl, —CF$_3$, or —CH$_3$; and the amine groups (NH$_2$) may be in the meta or para position with respect to R:

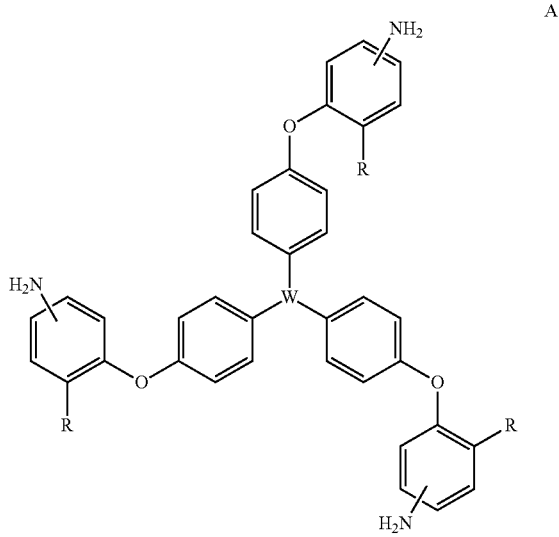

In one embodiment, a tetraamine crosslinker according to the present invention exhibits the following general structures B or C, in which X is C or Si:

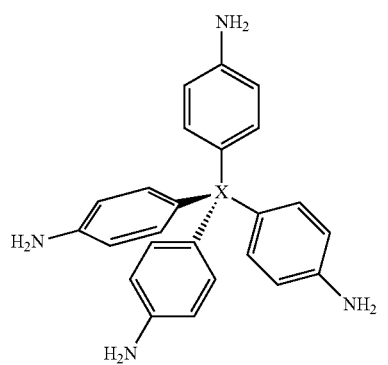

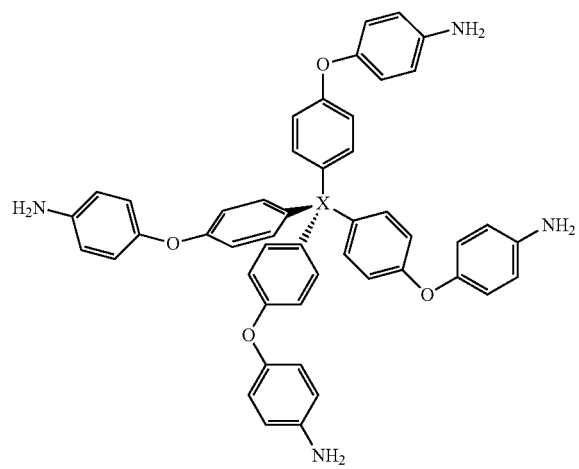

In another embodiment, a tetraamine crosslinker according to the present invention exhibits the following general structure D, in which Y is >C=O, —C(CF$_3$)$_2$—, —SO$_2$—, or —O—:

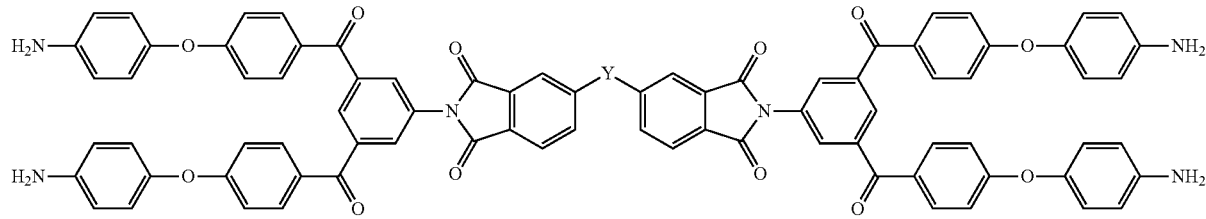

D

The present invention further includes methods of synthesizing triamine or trifunctional crosslinkers having the general structure A where W is CH$_3$C, N, or B(—O)$_3$, or P=O. FIG. 1 illustrates an exemplary method of making trifunctional crosslinkers according to the present invention starting from a tris(hydroxyphenyl) compound (I). Where W is CH$_3$C, N, B(—O)$_3$, or P=O, the tris(hydroxyphenyl) compound (I) may be 1,1,1-tris(4-hydroxyphenyl)ethane, tris(4-hydroxyphenyl)amine, tris(4-hydroxyphenyl)borate, or tris(4-hydroxyphenyl)phosphine oxide, respectively. A tris(nitrophenoxy)phenyl compound (III) is formed by mixing, in a polar, aprotic solvent, the tris(hydroxyphenyl) compound (I), a base such as potassium carbonate, and a halogenated nitrobenzene (II) having the following general structure:

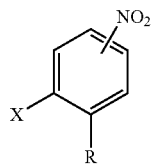

On the halogenated nitrobenzene compound (II), X is a halogen such as —F or —Cl; R is —H, —F, —Cl, —CF$_3$, or —CH$_3$; and the nitro group (—NO$_2$) is either meta or para with respect to R. In one embodiment, the halogenated nitrobenzene (II) is selected from the group consisting of 1-fluoro-4-nitro-benzene, 1-chloro-4-nitro-benzene, 1,2-difluoro-4-nitro-benzene, 1,2-dichloro-4-nitro-benzene, 1-fluoro-2-methyl-4-nitro-benzene, 1-chloro-2-methyl-4-nitro-benzene, 1-fluoro-2-(trifluoromethyl)-4-nitro-benzene, 1-chloro-2-(trifluoromethyl)-4-nitro-benzene, 1-methyl-2-chloro-4-nitrobenzene, 1-methyl-2-fluoro-4-nitro-benzene, 1-(trifluoromethyl)-2-chloro-4-nitro-benzene, 1-methyl-2-fluoro-4-nitro-benzene. Suitable examples of a polar, aprotic solvent may include dimethylformamide (DMF), N,N-dimethylacetamide (DMAc), and N-methylpyrrolidone (NMP). The method concludes with reduction of the tris(nitrophenoxy)phenyl compound (III) by catalytic hydrogenation in the presence of 5% palladium on activated carbon in a hydrogen atmosphere to form the trifunctional crosslinker (IV).

Figure 4:
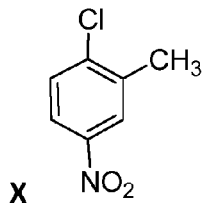
FIGS. 4 and 5 illustrate exemplary halogenated nitrobenzene compounds and trifunctional crosslinkers according to the present invention.
Figure 4:
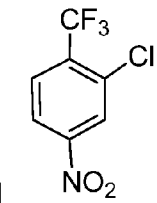
Figure 4:
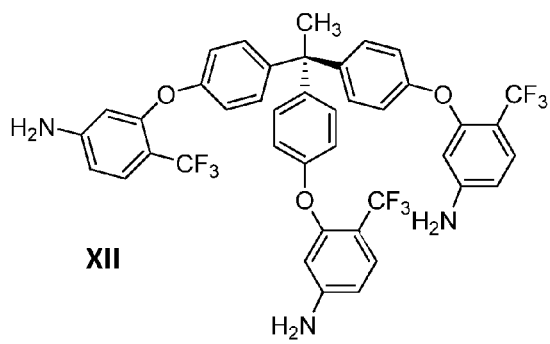
Figure 4:
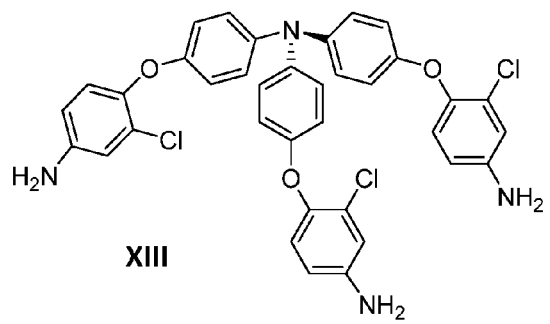
Figure 5:
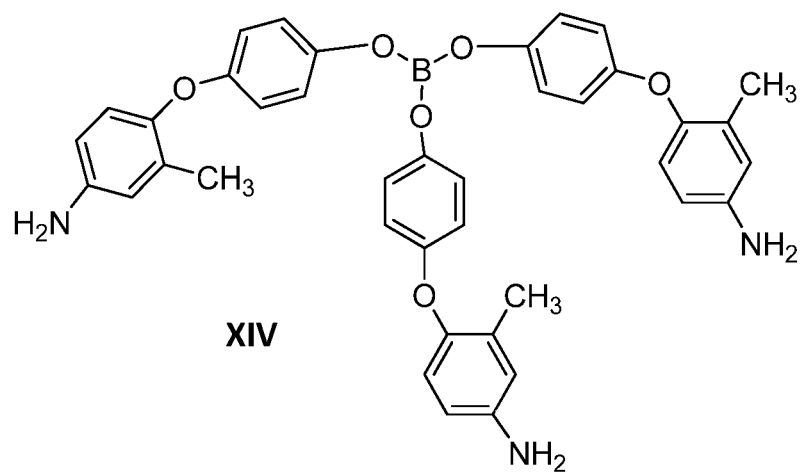
Figure 5:
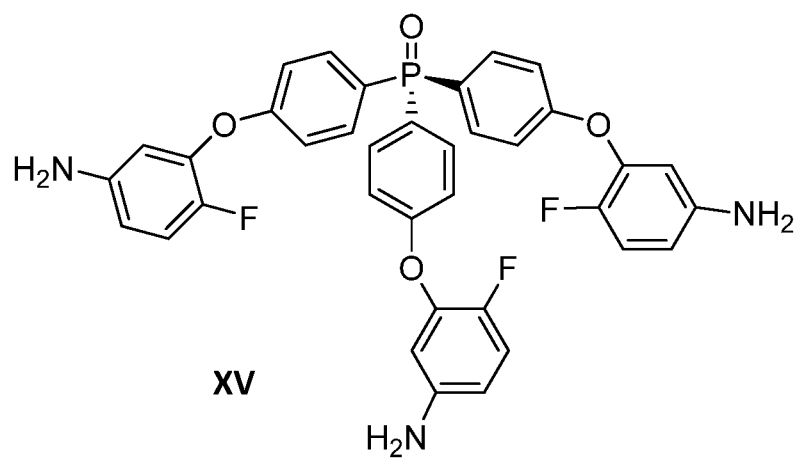

FIGS. 4 and 5 illustrate several exemplary compounds according to the present invention. In FIG. 4, compounds X and XI are exemplary halogenated nitrobenzene compounds that may be used to synthesize trifunctional crosslinkers according to the present invention. X is 1-chloro-2-methyl-4-nitro-benzene, in which R (—CH$_3$) is meta to the nitro group, while XI is 1-(trifluoromethyl)-2-chloro-4-nitro-benzenes, in which R (—CF$_3$) is para to the nitro group. In FIGS. 4 and 5, compounds XII-XV are exemplary trifunctional crosslinkers according to the present invention. XII is 1,1,1-tris[4-(2-trifluoromethyl-5-aminophenoxy)phenyl]ethane, in which W is CH$_3$C and R (—CF$_3$) is para to the primary amine (—NH$_2$) XIII is tris[4-(2-chloro-4-aminophenoxy)phenyl]amine, in which W is N and R (—Cl) is meta to the primary amine. XIV is tris[4-(2-methyl-4-aminophenoxy)phenyl]borate, in which W is B(—O)$_3$ and R (—CH$_3$) is meta to the primary amine. XV is tris[4-(2-fluoro-5-aminophenoxy)phenyl]phosphine oxide, in which W is P=O and R (—F) is para to the primary amine.

In another embodiment of the method, W is CH$_3$C, and the trifunctional crosslinker is selected from the group consisting of 1,1,1-tris[4-(2-fluoro-5-aminophenoxy)phenyl]ethane, 1,1,1-tris[4-(2-fluoro-4-aminophenoxy)phenyl]ethane, 1,1,1-tris[4-(2-chloro-5-aminophenoxy)phenyl]ethane, 1,1,1-tris[4-(2-chloro-4-aminophenoxy)phenyl]ethane, 1,1,1-tris[4-(2-trifluoromethyl-5-aminophenoxy)phenyl]ethane, 1,1,1-tris[4-(2-trifluoromethyl-4-aminophenoxy)phenyl]ethane, 1,1,1-tris[4-(2-methyl-5-aminophenoxy)phenyl]ethane, and 1,1,1-tris[4-(2-methyl-4-aminophenoxy)phenyl]ethane.

In another embodiment, W is N, and the trifunctional crosslinker is selected from the group consisting of tris[4-(4-aminophenoxyl)phenyl]amine, tris[4-(2-fluoro-5-aminophenoxy)phenyl]amine, tris[4-(2-fluoro-4-aminophenoxy)phenyl]amine, tris[4-(2-chloro-5-aminophenoxy)phenyl]amine, tris[4-(2-chloro-4-aminophenoxy)phenyl]amine, tris[4-(2-trifluoromethyl-5-aminophenoxy)phenyl]amine, tris[4-(2-trifluoromethyl-4-aminophenoxy)phenyl]amine, tris[4-(2-methyl-5-aminophenoxy)phenyl]amine, and tris[4-(2-methyl-4-aminophenoxy)phenyl]amine.

In yet another embodiment, W is B(—O)$_3$, and the trifunctional crosslinker is selected from the group consisting of tris[4-(4-aminophenoxyl)phenyl]borate, tris[4-(2-fluoro-5-aminophenoxy)phenyl]borate, tris[4-(2-fluoro-4-aminophenoxy)phenyl]borate, tris[4-(2-chloro-5-aminophenoxy)phenyl]borate, tris[4-(2-chloro-4-aminophenoxy)phenyl]borate, tris[4-(2-trifluoromethyl-5-aminophenoxy)phenyl]borate, tris[4-(2-trifluoromethyl-4-aminophenoxy)phenyl]borate, tris[4-(2-methyl-5-aminophenoxy)phenyl]borate, and tris[4-(2-methyl-4-aminophenoxy)phenyl]borate.

In a further embodiment of the method, W is P=O, and the trifunctional crosslinker is selected from the group consisting of tris[4-(4-aminophenoxyl)phenyl]phosphine oxide, tris[4-(2-fluoro-5-aminophenoxy)phenyl]phosphine oxide, tris[4-(2-fluoro-4-aminophenoxy)phenyl]phosphine oxide, tris[4-(2-chloro-5-aminophenoxy)phenyl]phosphine oxide, tris[4-(2-chloro-4-aminophenoxy)phenyl]phosphine oxide, tris[4-(2-trifluoromethyl-5-aminophenoxy)phenyl]phosphine oxide, tris[4-(2-trifluoromethyl-4-aminophenoxy)phenyl]phosphine oxide, tris[4-(2-methyl-5-aminophenoxy)phenyl]phosphine oxide, and tris[4-(2-methyl-4-aminophenoxy)phenyl]phosphine oxide.

Figure 3:
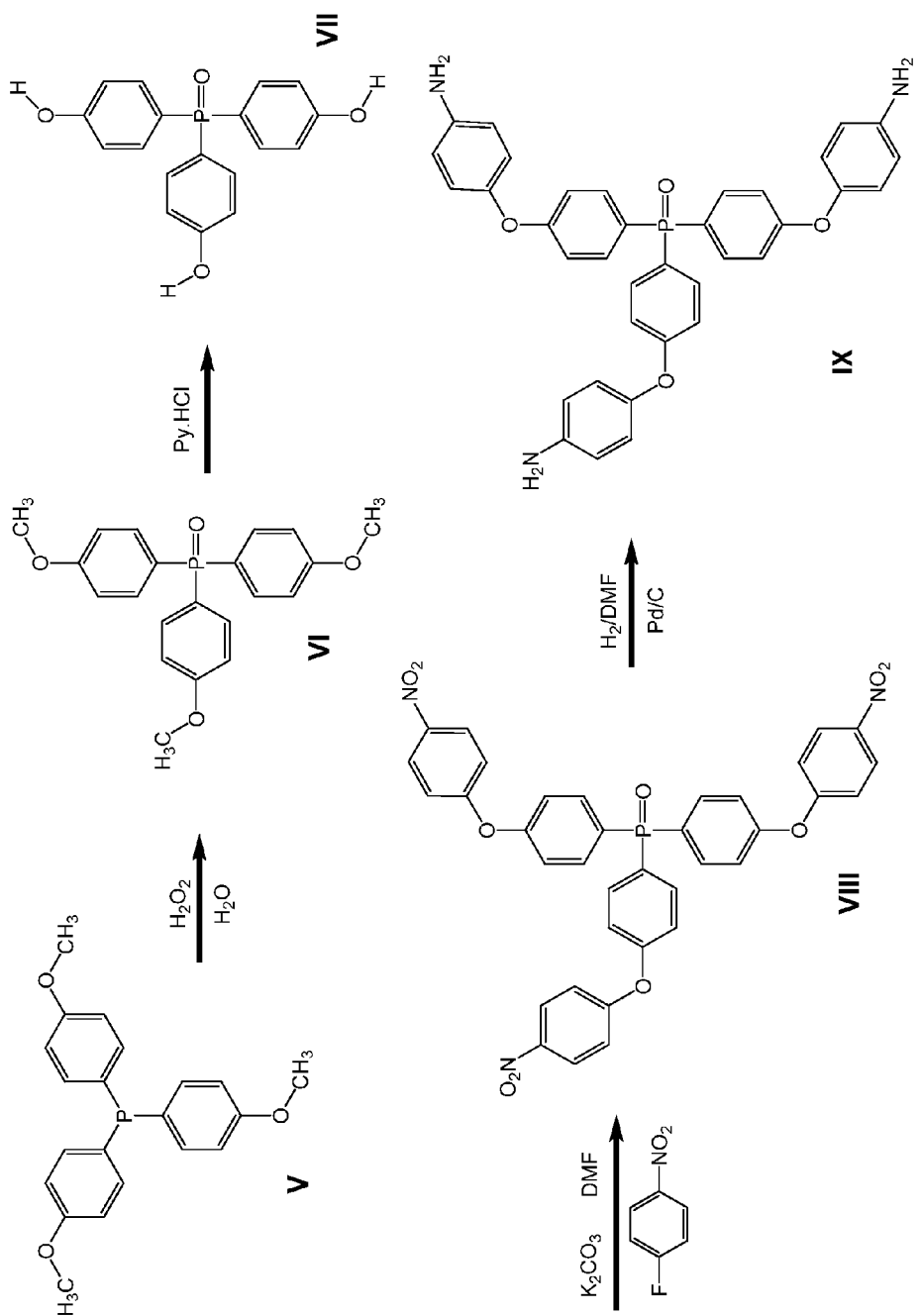
FIG. 3 illustrates the synthesis of another exemplary triamine crosslinker tris[4-(4-aminophenoxyl)phenyl]phosphine oxide (TNPO, IX) having the general structure A (W is P=O).

As shown in FIG. 3 and discussed in more detail in the Examples, where W is P═O, the present invention further includes additional steps to synthesize the tris(hydroxyphenyl) compound (I in FIG. 1). Tris(4-methoxyphenyl)phosphine (V) is oxidized with aqueous hydrogen peroxide to form tris(4-methoxyphenyl)phosphine oxide (VI). The tris(4-methoxyphenyl)phosphine oxide (VI) is then demethylated by heating in pyridine hydrochloride to form the tris(hydroxyphenyl) compound (I in FIG. 1), in this case tris(4-hydroxyphenyl)phosphine oxide (VII in FIG. 3). As shown in FIGS. 1 and 3, the tris(hydroxyphenyl) compound (I) i.e. tris(4-hydroxyphenyl)phosphine oxide (VII) is mixed with a halogenated nitrobenzene (II in FIG. 1; not separately labeled in FIG. 3) and potassium carbonate in a polar, aprotic solvent to form a tris(nitrophenoxy)phenyl compound (III in FIG. 1) i.e. a tris(nitrophenoxy)phenyl phosphine oxide compound (VII in FIG. 3), which is then reduced by catalytic hydrogenation in the presence of 5% palladium on activated carbon in a hydrogen atmosphere to form the trifunctional crosslinker (IV in FIG. 1; IX in FIG. 3).

Figure 2:
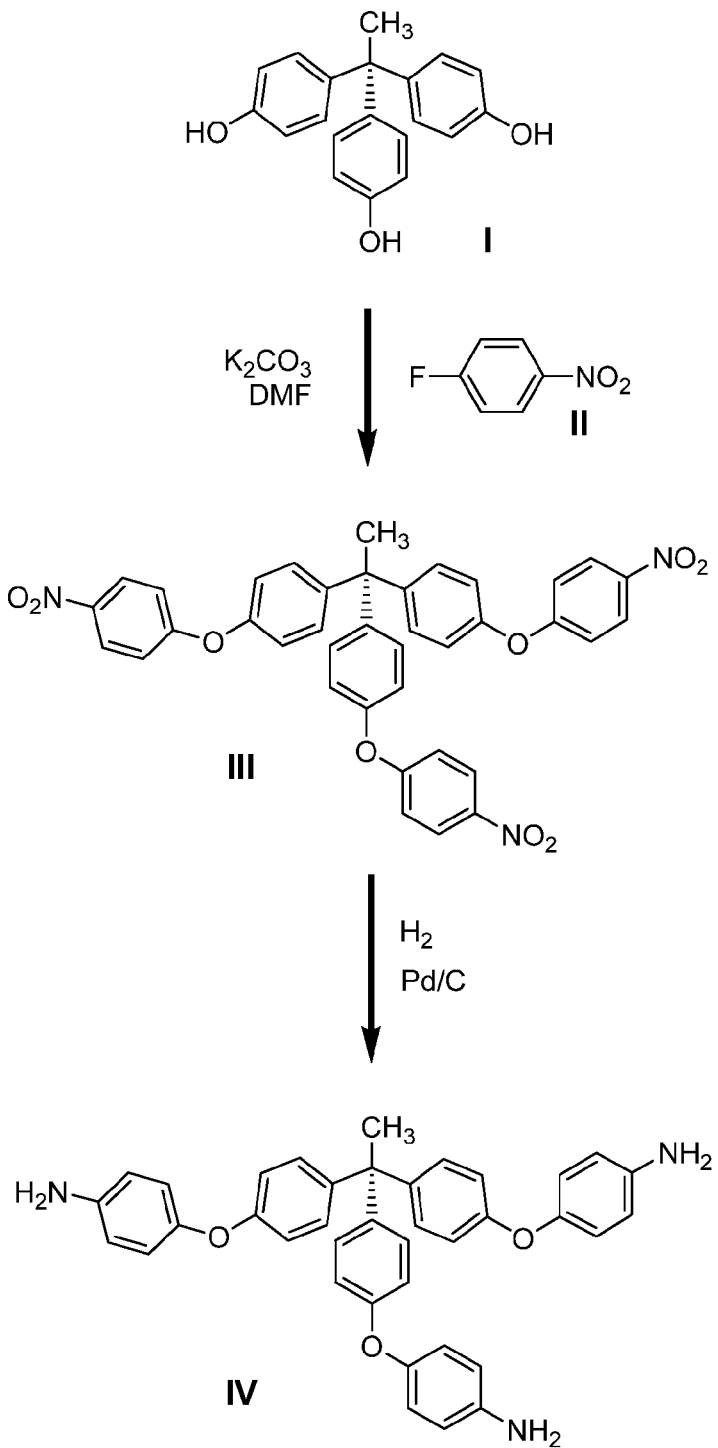
FIG. 2 illustrates the synthesis of an exemplary triamine crosslinker 1,1,1-tris[4-(4-aminophenoxyl)phenyl]ethane (TAPE, IV) having the general structure A (W is CH$_3$C).

As discussed in more detail in the Examples, FIG. 2 illustrates the synthesis of one specific exemplary triamine crosslinker—1,1,1-tris[4-(4-aminophenoxyl)phenyl]ethane (TAPE, IV)—having the general structure A in which W is $CH_3C$ and the halogenated nitrobenzene is 1-fluoro-4-nitrobenzene. FIG. 3 illustrates the synthesis of one specific exemplary triamine crosslinker—tris[4-(4-aminophenoxyl)phenyl]phosphine oxide (TNPO, IX)—having the general structure A in which W is P═O and the halogenated nitrobenzene is 1-fluoro-4-nitro-benzene.

The following examples and methods are presented as illustrative of the present invention or methods of carrying out the invention, and are not restrictive or limiting of the scope of the invention in any manner. Referring to the drawings, like reference numerals may designate like or corresponding parts throughout the several views.

Example 1

Synthesis of TNPE

The following is an exemplary procedure for the synthesis of one exemplary tris(nitrophenoxy)phenyl compound: 1,1,1-tris[4-(4-nitrophenoxyl)phenyl]ethane (TNPE, III) as depicted in FIG. 2. A tris(hydroxyphenyl) compound, which is 1,1,1-tris(4-hydroxyphenyl)ethane (THPE, I) (10.0 g, 33.0 mmol) in FIG. 2, a halogenated nitrobenzene, which is 1-fluoro-4-nitrobenzene (II) (15.4 g, 109 mmol) in FIG. 2, potassium carbonate (15.1 g, 109 mmol), and DMF (100 mL) were placed into a 250 mL three-necked flask equipped with a magnetic stir bar and nitrogen inlet and outlet. The mixture was stirred at room temperature for 24 hours and filtered. The filtrate was diluted with ethyl acetate (400 mL), and the organic layer was separated. The organic layer was washed with water three times. It was then dried over anhydrous magnesium sulfate and filtered. The filtrate was concentrated to 75 mL on a rotary evaporator and stored in a refrigerator for several days to afford 11.2 g (51%) of off-white crystals, m.p. 98-99° C. MS (m/e): 669 ($M^+$). Anal. Calcd. for $C_{38}H_{27}N_3O_9$: C, 68.18%; H, 4.06%; N, 6.27%; O, 21.50%. Found: C, 67.69%; H, 4.26%; N, 6.21%; O, 21.22%. FT-IR (KBr, $cm^{-1}$): 3076, 2979, 1586, 1513, 1486, 1344, 1248, 1165, 1107, 874, 846. $^1$H-NMR (DMSO-$d_6$, δ in ppm): 2.26 (s, 3H, $CH_3$), 7.17-7.27 (m, 18H, Ar—H), 8.28-8.31 (d, 6H, Ar—H).

Example 2

Synthesis of TAPE

The following is an exemplary procedure for the synthesis of an exemplary triamine crosslinker 1,1,1-tris[4-(4-aminophenoxyl)phenyl]ethane (TAPE, IV) by reduction of TNPE (III) via catalytic hydrogenation as depicted in FIG. 2. TNPE (III) (5.0 g, 7.5 mmol), THF (50 mL), and 5% palladium on activated carbon (0.50 g) were added to a hydrogenation bottle. The bottle was secured on a Parr hydrogenation apparatus, flushed three times with hydrogen, and then pressurized to 55 psi. After the mixture had been agitated at room temperature for 24 hours under the hydrogen pressure of 55 psi, it was filtered through Celite. The filter cake was washed with THF, and then the filtrate was evaporated to dryness on a rotary evaporator to afford a 4.25 g (98%) of yellow crystal, which was used without further purification, m.p. 220-221° C. MS (m/e): 579 ($M^+$). Anal. Calcd. for $C_{38}H_{33}N_3O_3$: C, 78.73%; H, 5.74%; N, 7.25%. Found: C, 78.17%; H, 5.78%; N, 7.04%. FT-IR (KBr, $cm^{-1}$): 3441, 3361 ($NH_2$), 3035, 2970, 1617, 1581, 1497, 1384, 1232, 1173, 1117, 1010, 871, 842. $^1$H-NMR (DMSO-$d_6$, δ in ppm): 2.02 (s, 3H, $CH_3$), 4.99 (s, 6H, $NH_2$), 6.53-6.58 (d, 6H, Ar—H), 6.68-6.74 (m, 12H, Ar—H), 6.88-6.93 (d, 6H, Ar—H).

Example 3

Synthesis of TMPO

The following is an exemplary procedure for the synthesis of tris(4-methoxyphenyl)phosphine oxide (TMPO, VI) as depicted in FIG. 3. Into a 100 mL three-necked flask equipped with a magnetic stir bar and nitrogen inlet and outlet were placed tris(4-methoxyphenyl)phosphine (TMP, V) (3.0 g, 8.5 mmol) and acetone (30 mL). A mixture of water (2 mL) and $H_2O_2$ (35%, 1 mL, 9 mmol) was added slowly. After the mixture had been stirred at room temperature for 1 hour, the acetone was evaporated, and methylene chloride (50 mL) was added. The organic phase was washed with a saturated NaCl solution (35 mL) three times with the aid of a separatory funnel. The organic layer was then dried over anhydrous sodium sulfate. Finally, the solvent was removed via rotary evaporation to afford 3.0 g (95%) of a white solid, m.p. 144.7-145.4° C. MS (m/e): 368 ($M^+$). Anal. Calcd. for $C_{21}H_{21}O_4P$: C, 68.47%; H, 5.75%; P, 8.41%. Found: C, 68.42%; H, 5.72%; P, 8.11%. FT-IR (KBr, $cm^{-1}$): 3068, 3026, 2959, 2837, 1597, 1569, 1503, 1468, 1289, 1254, 1179, 1121, 1019, 803, 671, 543. $^1$H-NMR (CDCl$_3$, δ in ppm): 3.84 (s, 6H, $CH_3$), 6.94-6.97 (dd, 6H, Ar—H), 7.54-7.60 (dd, 6H, Ar—H). $^{13}$C-NMR (DMSO-$d_6$, δ in ppm): 55.29, 114.08, 114.21, 124.19, 125.28, 133.21, 133.32, 161.79, 161.82.

Example 4

Synthesis of THPO

The following is an exemplary procedure for the synthesis of tris(4-hydroxyphenyl)phosphine oxide (THPO, VII) via demethylation of TMPO (VI) as depicted in FIG. 3. Into a 500 mL three-necked flask equipped with a magnetic stir bar and nitrogen inlet and outlet were placed TMPO (VI) (25.0 g, 67.9 mmol) and an excess of pyridine hydrochloride (250 g) at 210° C. for 2 hours. The light brown solution was poured into water while it was still hot. The white precipitate was collected and recrystallized from ethyl acetate to afford 21.0 g (95%) of white crystals, m.p. 274.8-276.8° C. MS (m/e): 326

(M+). FT-IR (KBr, cm$^{-1}$): 3380, 1601, 1581, 1505, 1436, 1278, 1175, 1119, 1068, 831, 677, 537. $^1$H-NMR (DMSO-d$_6$, δ in ppm): 6.86-6.89 (dd, 6H, Ar—H), 7.32-7.38 (dd, 6H, Ar—H), 10.14 (s, 3H, OH). $^{13}$C-NMR (DMSO-d$_6$, δ in ppm): 115.32, 115.45, 122.59, 123.69, 133.29, 133.40, 160.28, 160.30.

Example 5

Synthesis of TNPO

The following is an exemplary procedure for the synthesis of tris[4-(4-nitrophenoxy)phenyl]phosphine oxide (TNPO, XIII) as depicted in FIG. 3. Into a 250 mL three-necked flask equipped with a magnetic stir bar and nitrogen inlet and outlet were placed THPO (VII) (7.52 g, 20.0 mmol), 1-fluoro-4-nitrobenzene (II) (9.32 g, 66.0 mmol), potassium carbonate (9.14 g, 66.0 mmol), and DMF (100 mL) at 100° C. for 48 hours. The mixture was allowed to cool to room temperature and filtered. The filtrate was poured into water, and the precipitate was extracted with ethyl acetate (300 mL) three times with the aid of a reparatory funnel. The combined organic extract was concentrated under vacuum, and 13.3 g (97%) of yellow crystals that were formed during the concentrating process was collected by filtration, m.p. 205.0-206.6° C. MS (m/e): 689 (M+). FT-IR (KBr, cm$^{-1}$): 3071, 1612, 1585, 1523, 1487, 1345, 1242, 1176, 1116, 879, 866, 831, 788, 696, 556. $^1$H-NMR (DMSO-d$_6$, δ in ppm): 7.27-7.31 (d, 6H, Ar—H), 7.35-7.37 (d, 6H, Ar—H), 7.75-7.80 (m, 6H, Ar—H), 8.27-8.31 (d, 6H, Ar—H). $^{13}$C-NMR (DMSO-d$_6$, δ in ppm): 118.84, 119.82, 119.94, 126.22, 128.18, 129.23, 134.09, 134.20, 143.09, 157.93, 157.96, 161.29.

Example 6

Synthesis of TAPO

The following is a procedure for the synthesis of another exemplary triamine crosslinker tris[4-(4-aminophenoxyl)phenyl]phosphine oxide (TAPO, XIV) having the general structure A where W is P═O (IUPAC name 4,4',4"-(4,4',4"-phosphinetriyltris(benzene-4,1-diyl)tris(oxy))trianiline) by reduction of TNPO (XIII) via catalytic hydrogenation as depicted in FIG. 3. TNPO (VIII) (8.0 g, 11.6 mmol), DMF (120 mL), and 5% palladium on activated carbon (0.50 g) were added to a hydrogenation bottle. The bottle was secured on a Parr hydrogenation apparatus, flushed three times with hydrogen, and then pressurized to 60 psi. After the mixture had been agitated at room temperature for 24 hours under the hydrogen pressure of 60 psi, it was filtered through a cake of Celite. The filter cake was washed with DMF. The filtrate was then poured into water to precipitate a white solid that was subsequently recrystallized from ethanol/water to afford 6.41 g (98%) of white crystal, m.p. 211.1-211.5° C. MS (m/e): 559 (M+). Anal. Calcd. for $C_{36}H_{30}N_3O_4P$: C, 72.11%; H, 5.04%; N, 7.01%. Found: C, 72.01%; H, 4.97%; N, 6.91%. FT-IR (KBr, cm$^{-1}$): 3437, 3328, 3210, 3042, 1592, 1507, 1493, 1242, 1197, 1165, 1117, 871, 830, 671, 577. $^1$H-NMR (DMSO-d$_6$, δ in ppm): 5.06 (s, 6H, NH$_2$), 6.59-6.62 (d, 6H, Ar—H), 6.79-6.81 (d, 6H, Ar—H), 6.94-6.96 (d, 6H, Ar—H), 7.48-7.53 (d, 6H, Ar—H). $^{13}$C-NMR (DMSO-d$_6$, δ in ppm): 114.85, 115.89, 116.01, 121.34, 125.06, 126.13, 133.40, 133.51, 144.11, 146.13, 162.89, 161.92.

Example 7

Synthesis of a Crosslinked Polyimide

The following exemplary procedure demonstrates the utility of the presently disclosed triamine crosslinkers for the synthesis of crosslinked polyimide films. An exemplary fluorinated polyimide, CP2 (LaRC™-CP2, NASA Langley Research Center), was prepared by adding 1,3-bis(3-aminophenoxy)benzene (1.081 g, 3.700 mmol) and DMAc (14 mL) to a 50 mL three-necked flask equipped with a magnetic stirrer and a nitrogen inlet and outlet and stirred under dry nitrogen at room temperature for 30 minutes. An excess of 2,2-bis(phthalic anhydride)-1,1,1,3,3,3-hexafluoroisopropane (1.777, 4.000 mmol) was then introduced to the resulting solution. The light yellow solution was agitated at room temperature for 24 hours to afford a solution of poly(amic acid) oligomers (PAA oligomers). TAPE (IV) (0.1159 g, 0.200 mmol, 5 mol %) synthesized according to FIG. 2 and Examples 1 and 2 was added to the solution of PAA oligomers in DMAc. After the TAPE had completely dissolved, the resulting PAA sol-gel precursor solution was poured into a glass petri dish, followed by vacuum evaporation of the DMAc at 50° C. and heat-treatment according to following schedule: 100° C./2 hours, 150° C./2 hours, 175° C./1 hour, 200° C./2 hours, 250° C./1 hour, and 300° C./1 hour to form films consisting of xE-CP2. The resulting crosslinked polyimide films were approximately 20-100 μm in thickness. As compared to the T$_g$ of about 219° C. for neat polyimide (CP2, data not shown), the crosslinked CP2 films comprising 5 mol % TAPE demonstrated a higher T$_g$ of about 239° C.

Although this invention has been described with respect to certain preferred embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. A method for synthesizing a trifunctional crosslinker having the general structure:

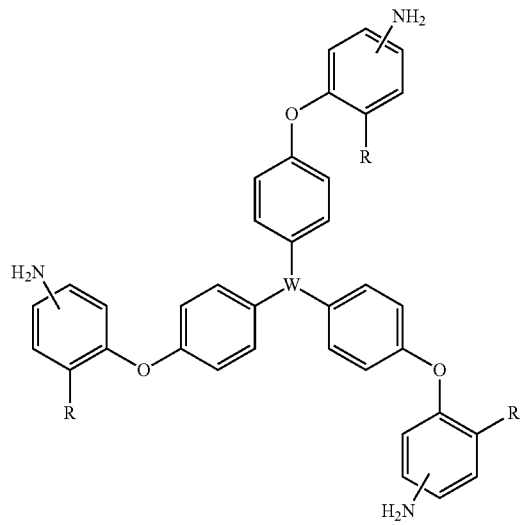

wherein W is N or B(—O)$_3$, and wherein the amine groups are located meta or para with respect to R, the method comprising the steps of:
mixing in a polar, aprotic solvent potassium carbonate, a tris(hydroxyphenyl) compound selected from the group consisting of tris(4-hydroxyphenyl)amine and tris(4-hydroxyphenyl)borate, and a halogenated nitrobenzene having the following general structure:

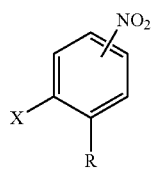

wherein X is selected from the group consisting of —F and —Cl; R is selected from the group consisting of —H, —F, —Cl, —CF$_3$, and —CH$_3$; and the nitro group is either meta or para with respect to R, to form a tris(nitrophenoxy)phenyl compound; and reducing the tris(nitrophenoxy)phenyl compound by catalytic hydrogenation in the presence of 5% palladium on activated carbon in a hydrogen atmosphere to form the trifunctional crosslinker.

2. The method of claim 1 wherein W is N, and wherein the trifunctional crosslinker is selected from the group consisting of tris[4-(4-aminophenoxyl)phenyl]amine, tris[4-(2-fluoro-5-aminophenoxy)phenyl]amine, tris[4-(2-fluoro-4-aminophenoxy)phenyl]amine, tris[4-(2-chloro-5-aminophenoxy)phenyl]amine, tris[4-(2-chloro-4-aminophenoxy) phenyl]amine, tris[4-(2-trifluoromethyl-5-aminophenoxy) phenyl]amine, tris[4-(2-trifluoromethyl-4-aminophenoxy) phenyl]amine, tris[4-(2-methyl-5-aminophenoxy)phenyl] amine, and tris[4-(2-methyl-4-aminophenoxy)phenyl]amine.

3. The method of claim 1 wherein W is B(—O)$_3$, and wherein the trifunctional crosslinker is selected from the group consisting of tris[4-(4-aminophenoxyl)phenyl]borate, tris[4-(2-fluoro-5-aminophenoxy)phenyl]borate, tris[4-(2-fluoro-4-aminophenoxy)phenyl]borate, tris[4-(2-chloro-5-aminophenoxy)phenyl]borate, tris[4-(2-chloro-4-aminophenoxy)phenyl]borate, tris[4-(2-trifluoromethyl-5-aminophenoxy)phenyl]borate, tris[4-(2-trifluoromethyl-4-aminophenoxy)phenyl]borate, tris[4-(2-methyl-5-aminophenoxy)phenyl]borate, and tris[4-(2-methyl-4-aminophenoxy)phenyl]borate.

4. A method for synthesizing a trifunctional crosslinker having the general structure:

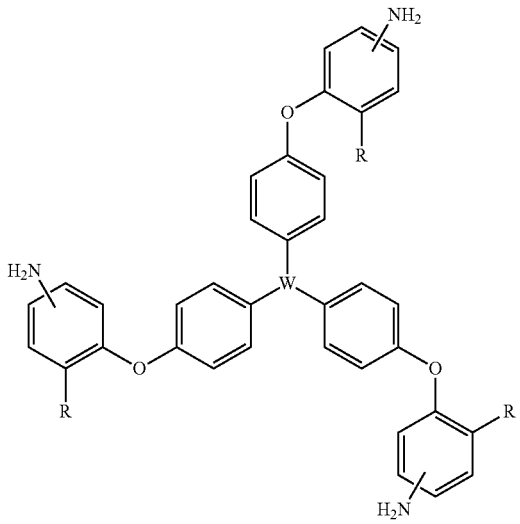

wherein W is P═O and wherein the amine groups are located meta or para with respect to R, the method comprising the steps of:

oxidizing tris(4-methoxyphenyl)phosphine with aqueous hydrogen peroxide to form tris(4-methoxyphenyl)phosphine oxide;

demethylating the tris(4-methoxyphenyl)phosphine oxide by heating in pyridine hydrochloride to form tris(4-hydroxyphenyl)phosphine oxide;

mixing in a polar, aprotic solvent the tris(4-hydroxyphenyl)phosphine oxide, potassium carbonate, and a halogenated nitrobenzene having the following general structure:

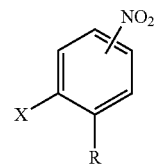

wherein X is selected from the group consisting of —F and —Cl; R is selected from the group consisting of —H, —F, —Cl, —CF$_3$, and —CH$_3$; and the nitro group is either meta or para with respect to R, to form a tris(nitrophenoxy)phenyl phosphine oxide compound; and reducing the tris(nitrophenoxy)phenyl phosphine oxide compound by catalytic hydrogenation in the presence of 5% palladium on activated carbon in a hydrogen atmosphere to form the trifunctional crosslinker.

5. The method of claim 4 wherein the halogenated nitrobenzene is selected from the group consisting of 1-fluoro-4-nitro-benzene, 1-chloro-4-nitro-benzene, 1,2-difluoro-4-nitro-benzene, 1,2-dichloro-4-nitro-benzene, 1-fluoro-2-methyl-4-nitro-benzene, 1-chloro-2-methyl-4-nitro-benzene, 1-fluoro-2-(trifluoromethyl)-4-nitro-benzene, 1-chloro-2-(trifluoromethyl)-4-nitro-benzene, 1-methyl-2-chloro-4-nitrobenzene, 1-methyl-2-fluoro-4-nitro-benzene, 1-(trifluoromethyl)-2-chloro-4-nitro-benzene, 1-methyl-2-fluoro-4-nitro-benzene.

6. The method of claim 4 wherein the trifunctional crosslinker is selected from the group consisting of tris[4-(4-aminophenoxyl)phenyl]phosphine oxide, tris[4-(2-fluoro-5-aminophenoxy)phenyl]phosphine oxide, tris[4-(2-fluoro-4-aminophenoxy)phenyl]phosphine oxide, tris[4-(2-chloro-5-aminophenoxy)phenyl]phosphine oxide, tris[4-(2-chloro-4-aminophenoxy)phenyl]phosphine oxide, tris[4-(2-trifluoromethyl-5-aminophenoxy)phenyl]phosphine oxide, tris[4-(2-trifluoromethyl-4-aminophenoxy)phenyl]phosphine oxide, tris[4-(2-methyl-5-aminophenoxy)phenyl]phosphine oxide, and tris[4-(2-methyl-4-aminophenoxy)phenyl]phosphine oxide.

\* \* \* \* \*